United States Patent [19]

Harder et al.

[11] Patent Number: 4,712,541
[45] Date of Patent: Dec. 15, 1987

[54] BONE NAIL AND INSTRUMENTS FOR THE TREATMENT OF FRACTURES

[75] Inventors: Hans E. Harder, Probsteierhagen; Hermann Kramer, Neumunster, both of Fed. Rep. of Germany

[73] Assignee: Howmedica International, Inc., Kiel, Fed. Rep. of Germany

[21] Appl. No.: 943,970

[22] Filed: Dec. 19, 1986

Related U.S. Application Data

[63] Continuation of Ser. No. 493,887, May 12, 1983, abandoned.

[30] Foreign Application Priority Data

May 18, 1982 [DE] Fed. Rep. of Germany ... 8214493[U]
Mar. 18, 1983 [EP] European Pat. Off. ........ 83102694.3

[51] Int. Cl.⁴ ............................................... A61F 5/04
[52] U.S. Cl. ................................................ 128/92 YY
[58] Field of Search ............................. 623/11, 16, 18; 128/92 YY, 92 YZ

[56] References Cited

U.S. PATENT DOCUMENTS

| | | | |
|---|---|---|---|
| 2,781,758 | 2/1957 | Chevalier | 623/23 |
| 2,934,065 | 4/1960 | Townley | 623/23 |
| 3,433,220 | 3/1969 | Zickel | 128/92 YY |
| 4,169,470 | 10/1979 | Ender et al. | 128/92 YZ |

FOREIGN PATENT DOCUMENTS

| | | | |
|---|---|---|---|
| 2484243 | 12/1981 | France | 128/92 YY |
| 576249 | 6/1976 | Switzerland | 128/92 YZ |

*Primary Examiner*—Richard J. Apley
*Assistant Examiner*—David J. Isabella
*Attorney, Agent, or Firm*—Charles J. Knuth; Peter C. Richardson; Lawrence C. Akers

[57] ABSTRACT

A bone nail for the treatment of fractures in the proximal femur zone is disclosed having a distal end portion adapted to be disposed at the outer surface of the femoral condyle, said end portion being provided with a coupling portion for engagement with a driving tool, a proximal end portion adapted to be seated in the proximal femur, and an arcuately curved portion between the ends, with the proximal end portion being provided with a rounded-off thickened portion at the free end thereof.

4 Claims, 13 Drawing Figures

BONE NAIL AND INSTRUMENTS FOR THE TREATMENT OF FRACTURES

This is a continuation of application Ser. No. 493,887 filed on May 12, 1983, now abandoned.

BACKGROUND OF THE INVENTION

The invention relates to a bone nail for the treatment of fractures in the proximal femur zone, comprising a distal end portion disposed at the outer surface of the femoral condyle, said end portion being provided with a coupling portion for engagement with a driving tool, a proximal end portion seated in the proximal femur and an arcuately curved portion between the ends.

Such a nail is known (West German Pat. No. 23 41 439; West German Utility Model No. 7 218 224). It is normally used together with several such nails (bunch nailing). The individual bone nails consisting of metal are provided with a diameter such that they are sufficiently elastic, so that they may be driven into the medullary canal of the femur via a window in the condyle of the femur. The proximal end of the nail seeks its way in the medullary canal and arrives in the femoral head via the femoral neck. The distal end of the nail is designed in such a manner that it is adapted to be brought into engagement with a drive-in tool. The bone nail is driven onward in the medullary canal with the aid of the drive-in tool while being watched on an image amplifier, with the first nail in particular having to be more or less rotated for repositioning the bone fragments. The powerful engagement of the drive-in tool at the distal end of the nail, thus, must be in a position also to transfer a substantial amount of torque onto the nail.

The known bone nails suffer from some disadvantages. The flattenings at the distal end which are oriented transversely to the axis of curvature and which are in addition provided with an aperture for the purpose of obtaining an effective engagement of a drive-in tool, may be effective in the manner of a chisel if they do not come to lie completely flat against the bone and in parallel therewith, respectively. The relatively sharp edges formed in this manner may have an irritating effect on the adjacent tissue. As the flattenings are normally formed in an upsetting process, additional processing is required so as to remove any burrs or sharp edges formed in said upsetting step. Through the flattening of a round nail cross sectional area, in addition, a critical zone of transition will form having a relatively high notch effect, so that with a considerable amount of torque applied at the distal end a plastic deformation or even a shearing off may be the result in this zone. Upon rotation of the distal ends against each other, several flattened distal ends require a relatively great amount of space, whereby the well-being of the patent may be affected.

So that the known nail bones may be driven onward more easily in the medullary canal it is known to taper them at the proximal end. Owing thereto, however, the danger exists that the proximal ends in the neck or in the head zone may protrude and enter the hip bone and the acetabulum, respectively, which is to be considered to be a serious complication of the method of treatment rendering it ineffective.

SUMMARY OF THE INVENTION

It is therefore the object of the invention to provide a bone nail for the treatment of fractures in the proximal femoral zone by which it is ensured that inadvertent injuries of the bone in the zone of the proximal femur will not occur.

This object is attained in accordance with the invention in that the proximal end portion at the free end is provided with a rounded-off thickening. Even though such a thickening doubtless increases the power of driving-in for the individual nail, this may, on the other hand, be readily taken into bargain because, with the measure according to the innovation it is avoided that the proximal end of the nail when being threaded into the neck or head zone of the femur, injures the femur in that zone by penetrating into, and through the corticalis, respectively. The increased driving power, in relation to that one necessary with a point at the proximal end, lies nevertheless within a range which, with the up to now usual operational techniques for such bone nails may doubtless be accepted.

It goes without saying that the thickening is uniformly rounded in order to avoid injuries. According to one embodiment of the invention, the thickening is formed in the manner of a bead. It is preferably provided by upsetting the proximal nail end.

The plane of curvature of the bone nail lies approximately in the plane extending between the femur shank and the femur neck. The introduction of forces into the implanted nail essentially is in parallel with the femur shank and thus onto the proximal end of the nails, thereby exerting on the curved proximal end portion a torque in the plane of the curvature. The load on the nails thus is largely a bending load. For this reason, a pointed proximal end has a negative effect, because only a small area is provided for the engagement of forces. Likewise, in this regard a thickening at the proximal end brings about an improvement, with the area available for the engagement of forces being substantially increased. In this connection provision is made in another embodiment of the invention for a flattening to be provided at the free end of the thickening, the plane of which extends at an angle with respect to the axis of the proximal nail end in such a manner that it lies approximately normal to the direction of loading. That means that the flattening, the areal dimension of which may obtain a considerable measure relative to the nail cross sectional area, approximately lies normal to the femur axis and thus also normal to the direction of loading.

The known bone nails are circular in cross section. For the moment of resistance the bone nails are required to provide, however, the nail diameter in the plane of curvature is largely decisive. That means that the nail may be reduced in a direction normal to the axis of curvature, without thereby substantially influencing the moment of resistance. With nail cross sectional areas formed in this manner, quite a considerable reduction of nail material may be achieved. In this connection, provision is made in another embodiment of the invention for the cross sectional area of the nail to be polygonal over the length thereof with edges rounded off. But here, preferably, the main axis lies in the plane of curvature. In another embodiment of the invention it is proposed in this connection that the cross sectional area be triangular, preferably in the form of an equilateral triangle. With this cross sectional shape too, material is saved without markedly reducing the moment of resistance vis-a-vis a nail having a comparable circular cross sectional area. As the edges of the triangular cross sectional area are markedly rounded off, there exists also no danger of injury in the medullary canal. It is furthermore also readily guaranteed that the nail may be rotated for purposes of repositioning and driving-in. A triangular cross sectional configuration, however, offers the additional advantage that narrower packaging is possible than with a circular cross sectional configuration, so that in a given case more nails may be driven in than bone nails having a circular cross sectional configuration. The overall moment of resistance with a given cross sectional area of the medullary canal may be adjusted to be higher than with round nails.

In another embodiment of the invention provision is made for lying in the axis of curvature. With such a cross sectional configuration the saving of material is still greater.

A space-saving arrangement of the distal nail ends results if the radial extention of the distal end does not exceed that one of the remaining nail, i.e. the outer contour of the nail does not enlarge in the distal end zone. In this connection provision is made in another embodiment of the invention for a bore to be provided at the distal end, preferably a throughbore, the axis of which preferably lies in the plane of curvature. A portion of the drive-in tool may be brought into engagement with the bore, so that a torsion may be applied to the distal nail end.

Alternatively, it is proposed according to another embodiment of the invention that a recess be formed spaced through a distance from the distal end so as to form a clamping section of a polygonal cross sectional shape. With a polygonal cross sectional shape of the nail a recess would not be necessary in view of the application of a rotational force. A recess, however, offers the advantage that effective pull-out forces may be applied thereby also onto the nail.

Advantageous further emobodiments of a set of instruments according to the invention for driving-in the nail according to the invention are indicated in further subclaims.

DETAILED DESCRIPTION OF THE INVENTION

Some examples of embodiments of the invention are going to be described in the following in more detail by way of drawings.

Figure 1:
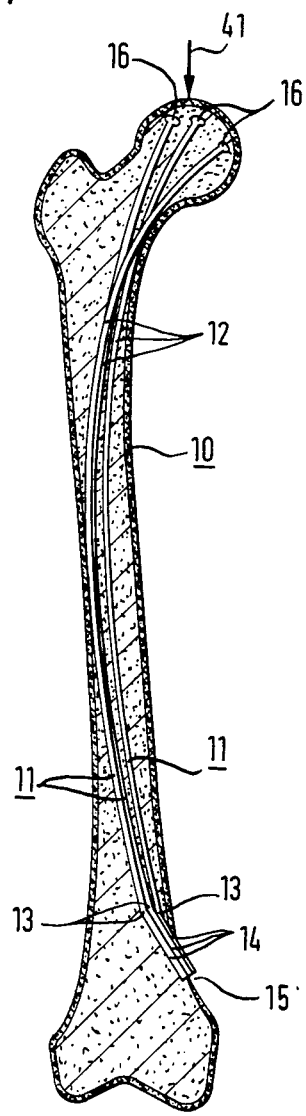
FIG. 1 shows a sectional view of a femur having three nails according to the invention implanted therein.

Prior to enlarging on the individual representations shown in the drawings let it be stated that each of the features described and shown is of inventively essential importance by itself or in connection with features of the claims.

The three bone nails implanted in a femur 10 are generally referenced 11. They are provided with a continuous curvature starting out from the proximal end, as shown at 12. In the zone of the distal end a bend 13 is formed which is followed by a straight piece 14. The bone nails 11 have been driven in via a window 15 of the medial condyle of the femur 10 as shown, with the aid of a drive-in tool i.e. one bone nail after the other. The nail first driven in normally serves to reposition the segment of fracture. The introduction of the bone nails is performed under control with the aid of an image amplifier, so that a fanning out may be obtained in the head region of the femur, thereby achieving a certain rotary stability of the head relative to the remaining femur. The proximal end portions are provided with thickenings, generally referenced 16 in FIG. 1.

Figure 3:
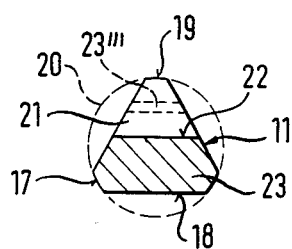
FIG. 3 shows a sectional view of the nail according to FIG. 2 taken on line 3—3.

As may be recognized from FIG. 3, the cross sectional configuration of the nails 12 is an equilateral triangle, having the edges thereof considerably rounded off at the corners as shown at 17. One side 18 in this arrangement forms the convex side of the curvature 12, while the opposite edge 19 is disposed on the concave site of the nail 11.

As indicated by the circle 20 drawn in broken lines, the nail 11 brings about a considerable material saving as opposed to a nail having a circular cross sectional area 20, without the moment of resistance being substantially reduced. The cross section configuration shown in FIG. 3, in addition, offers the advantage that the nails may be better "packed" in the medullary canal.

Figure 2:
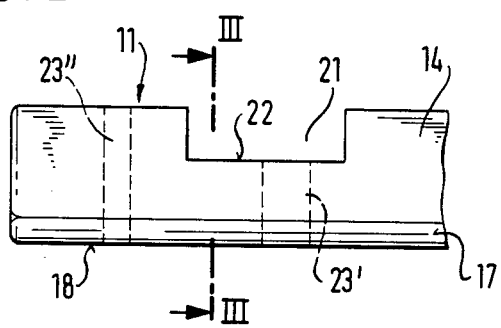
FIG. 2 shows a lateral view of the distal end of a bone nail according to FIG. 1.

As is furthermore to be derived from FIGS. 2 and 3, a recess 21 is formed in the straight distal end portion 14 the bottom surface of said recess extending approximately in parallel with the side 18 of the nail 11. A drive-in tool may be brought into engagement with the recess 21 in order to drive the nail forward in the medullary canal or extract it from the medullary canal, and perform during these movements, in addition, a rotary movement. The remaining cross sectional area 23 easily suffices to withstand forces of rotation. In this arrangement, it is recommendable to select the transition of the cross sectional area 23 into the triangular full cross sectional area to be a steady one, so as to avoid unnecessarily high notching forces.

It will be noted from FIGS. 2 and 3 that despite a coupling section for a drive-in tool the outer contour of the remaining nail is not departed from, therefore, there are no projecting parts unnecessarily increasing the space and affecting the tissue.

Figure 4:
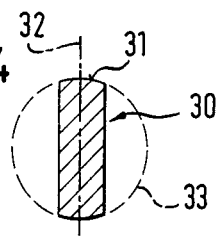
FIG. 4 shows another profile of a bone nail according to the invention.

FIG. 4 shows a bone nail 30 in a cross sectional view which is approximately rectangularly shaped with edges 31 likewise strongly rounded off. The plane of curvature coincides with the major axis 32 of the rectangular cross sectional configuration. The bone nail 30 has a moment of resistance comparable to that of a bone nail having a circular cross sectional configuration as indicated by the circle 33 shown in broken lines. The former, therefore has for a result a considerable material saving without the bearing capacity thereby being reduced.

Figure 5:
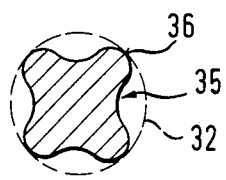
FIG. 5 shows a further profile of a bone nail according to the invention.

FIG. 5 shows a nail 35 approximately having the shape of a Maltese cross in cross section, with the edges again being strongly rounded off as shown at 36. Here as well a circle 37 shown in broken lines shows a circular cross section of a bone nail having a moment of resistance which is comparable to that of the bone nail 35.

Figure 6:
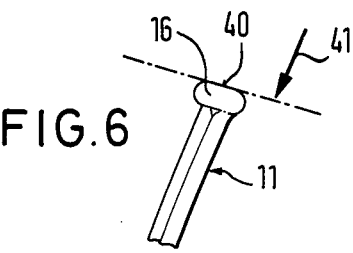
FIG. 6 shows an example of embodiment of a proximal end of the bone nail according to FIG. 1.

In FIG. 6, the bone nail 11 is shown with the proximal end portion. There will be recognized a bead 16 of enlarged diameter having an approximately circular outer contour. Furthermore, the bead is flattened at the free end thereof, as shown at 40. This flattening lies in a plane which extends approximately vertically with respect to the direction of loading which is indicated by an arrow 41. Said arrow 41 is also shown in FIG. 1.

It goes without saying that additionally the portion 23 is provided with a bore or throughbore 23', respectively, in order to improve the power engagement with a drive-in tool. A throughbore at the distal end may, by the way, be shaped with any cross sectional configuration, in order to have a drive-in and extraction tool engage thereat.

In FIG. 2 a bore is indicated at 23" which is arranged outside the recessed portion 21 facing the end. A bore arranged transversely thereto is designated with 23'" in FIG. 3.

The nail has, besides, a straight portion at the distal end portion which is connected to the remaining nail through a wide arc.

Figure 7:
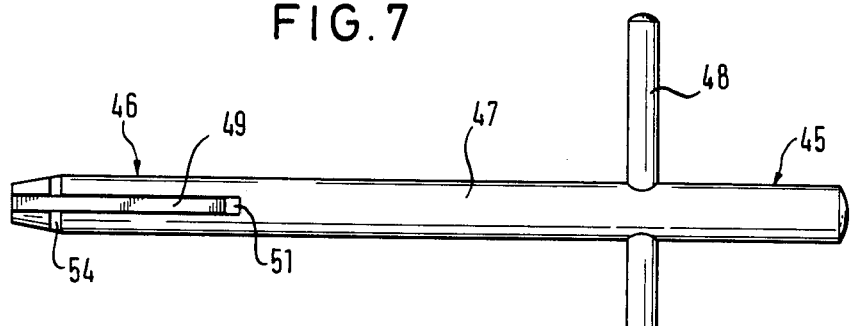
FIG. 7 shows a fore-stroke apparatus for a bone nail according to the invention.
Figure 8:
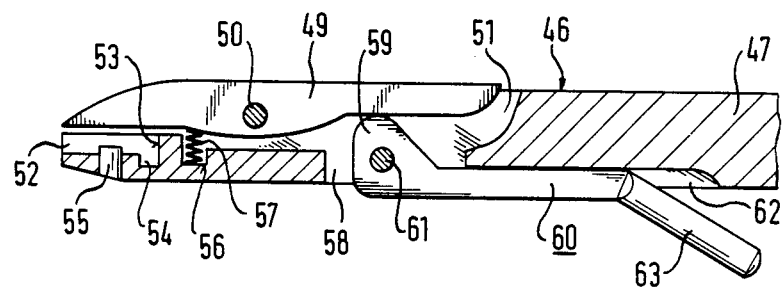
FIG. 8 shows a sectional view of the front portion of the apparatus according to FIG. 7.
Figure 9:
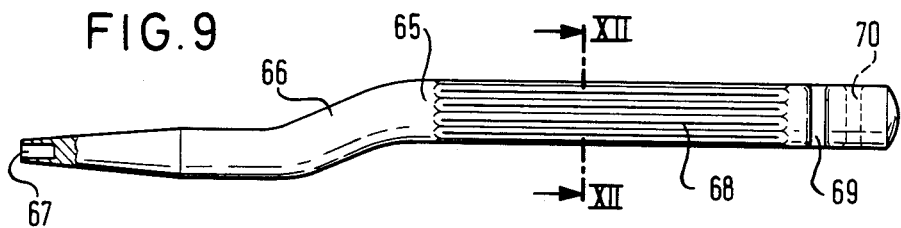
FIG. 9 shows an after-stroke apparatus for a bone nail according to the invention.

FIGS. 7 and 8 show a fore-stroke drive-in apparatus for bone nails shown in FIGS. 1 to 6. Said apparatus consists of a gripping portion 45 and a coupling portion 46. Both of them comprise an elongated shank 47 of a circular cross sectional configuration provided with a transverse bar 48 in the gripping portion 45 which is guided through a corresponding bore. A coupling lever 49 is pivotally supported in the coupling portion 46 (FIG. 8) with the aid of a bearing pin 50. For the purpose of accommodating the coupling lever 49 a slot 51 is formed axially in the shank 47 which accommodates the relatively narrow coupling lever 49, so that it projects but little over the outer contour of the shank. The coupling lever 49 extends as far as the end of the shank 47 spanning a recess 52 of triangular cross sectional configuration which opens towards the end of the shank 47 and is defined by an abutment wall 53 at the opposite end having a transverse groove 54 situated at the foot portion thereof. A journal 55 recessed into the shank 47 projects upwards into the recess 52.

A blind bore 56 is provided in the bottom of the slot 51 which accommodates a compression spring 57 biasing the coupling lever 49 in a clockwise sense. The slot 51 is provided with an interruption 58 in a diametrically downward direction for the accommodation of a cam 59 of a clamping lever 60. The clamping lever 60 is pivotally supported in the region of the cam 59 with the aid of a bearing journal 61, said levers 49 and 60 being pivotable approximately in one and the same plane. A center portion of the lever 60 is in part accommodated in a recess 62 of the shank 47. A handling means 63 extends obliquely outwards.

In the position as shown in FIG. 8 the coupling lever 49 is locked by the clamping lever 60. The highest point of the cam 59 is disposed opposite to the axis of rotation of the journal 61 in offset arrangement with respect to the pivotal journal 50. The spring 57 tends to rotate the coupling lever 49 in a clockwise direction. Thereby, the portion of the lever 49 shown to the right in FIG. 8 exerts a pressure on the cam 59 from above and biases the clamping lever 60 in a counterclockwise direction. A pivotal movement of the clamping lever 60 in this direction, however, is not possible because it is limited by the shank 57 and the recess 62, respectively. Only when the handling means 63 is engaged by hand and the clamping lever 60 is likewise rotated in a clockwise direction may the coupling lever 59 likewise pivot in a clockwise direction. Thereby the distal end of a bone nail may be inserted into the recess 42 with the journal 55, for example, engaging in the recess 21 of a bone nail according to FIGS. 1 to 3. A bone nail thus accommodated may now be driven in with the aid of the fore-stroke tool according to FIGS. 7 and 8 and be manipulated in the manner as desired and may, for example, also be withdrawn again entirely or in part. An inadvertent loosening of the apparatus from the bone nail is avoided by the clamping device as described above.

Figure 10:
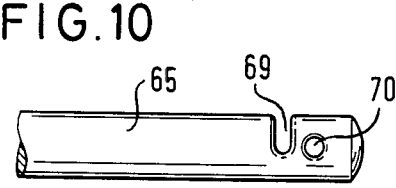
FIG. 10 shows a view of the rear end of the apparatus according to FIG. 9 rotated through 90°.
Figures 11, 12:
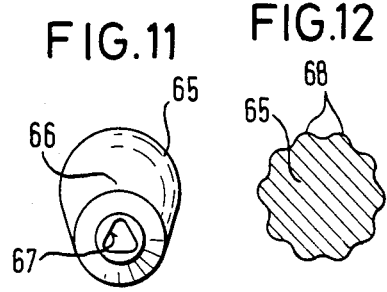
FIG. 11 shows a front view of the apparatus according to FIG. 9.
FIG. 12 shows a sectional view of the apparatus according to FIG. 9 taken on line 12—12.

As it is difficult especially with several nails to wholly drive-in the bone nail with the aid of the fore-stroke drive-in apparatus according to FIGS. 7 and 8, an after-stroke apparatus is provided in accordance with FIGS. 9 to 12. The after-stroke apparatus comprises an elongated shank 65 of an approximately circular-shaped cross sectional configuration which is slightly cranked at 66 in the region of the forward third thereof. The shank 66 tapers steadily towards the front end. At the front end thereof it is provided with a forwardly opening recess 67 the cross section of which is adapted to the cross section of the distal end, i.e. is triangularly shaped, for example, as shown in FIG. 11. The gripping portion proper is provided with longitudinally extending corrugations 68, so that the after-stroke apparatus may be better seized by hand. In the rearward zone thereof the shank 65 has an outward opening transversely extending slot 69 formed therein. A throughbore 70 is furthermore provided to extend in parallel therewith (FIG. 10). The slot 69 and the throughbore 70 respectively have a width and diameter slightly greater than the greatest diameter of the bone nail. The apparatus according to FIGS. 9 to 12 may therefore also serve as a so-called setting iron with the aid of which it is possible to deform the bone nail in a limited way, that is to impart thereto a different curvature, for example, or a different direction. Preferably, two such apparatuses are employed in this operation.

The point of the after-stroke apparatus may be provided with a milling or flattening at the underside thereof so as to be able to engage within the groove 21 of the nail 11 for purposes of beating out. In this manner the implanted nail may be beaten out so far that the fore-stroke drive-in tool may be employed.

Figure 13:
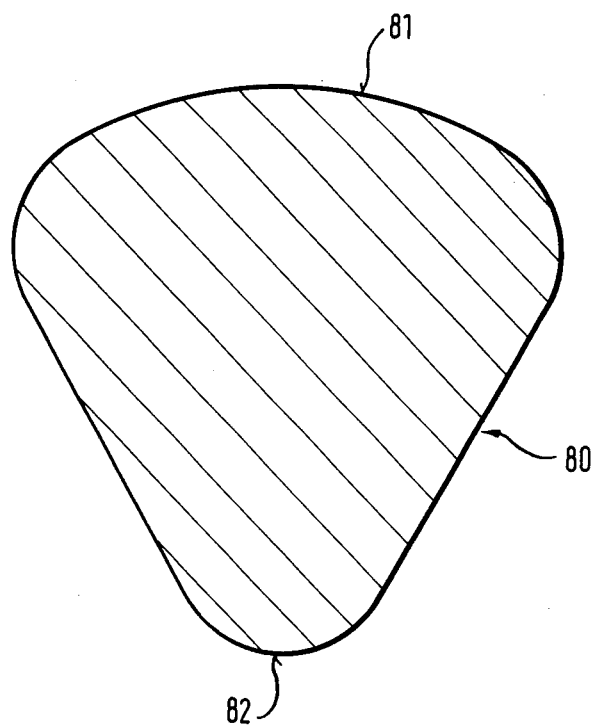
FIG. 13 shows a cross sectional view of another embodiment of a nail.

The profile of the nail 80 according to FIG. 13 is indeed likewise triangularly shaped, on principle, as is the one according to FIGS. 1 to 3. The convex side 81, however, is not straight but is crowned in cross section. The relatively large radius of the side 81 results in a soft transition towards the radii at the edges of the nail 80. Also the concavely extending edge 82 is provided with a radius.

We claim:

1. A thin, elongated flexible and resilient bone nail, having a longitudinal axis and having a substantially uniform cross-section along the length thereof, for the treatment of fractures in the proximal femur zone, comprising a distal end portion adapted to be disposed at the outer surface of the femoral condyle and having a free end terminating in a distal tip of the nail, a proximal end portion adapted to be seated in the natural femoral head and having a free end, and a curved intermediate portion between said end portions, with said proximal end portion being provided at the free end thereof with a rounded-off thickened portion and with the cross-sectional configuration of said distal end portion of the nail being polygonal with edges rounded off and identical to the cross-sectional configuration of the remainder of the nail, except for said rounded-off thickened portion and a recess in said distal end portion formed by a solid polygonal cutout having a bottom surface substantially parallel to said longitudinal axis and a plurality of additional surfaces coincident with a partial perimeter of said polygonal cross-section, said recess forming a reduced gripping portion which is polygonal in cross section for engagement with a driving tool and said recess being spaced from the distal tip of the nail by a length.

2. A bone nail of claim 1 wherein said nail is configured to lie substantially within a single plane of curvature and a throughbore is provided at the distal end of said nail, the axis of which throughbore is disposed in said plane of curvature of said nail.

3. A bone nail of claim 1 wherein said nail is configured to lie substantially within a single plane of curvature, said intermediate portion is continuously curved concavely towards a direction that is substantially the medial direction when the nail is implanted and the cross sectional configuration of said nail is an equilateral triangle with edges rounded off having an axis disposed in said plane of curvature of the nail extending from an apex located on the medial side of the nail, with the cross section in said reduced gripping portion being a four-sided figure coincident with said equilateral triangle but excluding a medial triangular area including said apex.

4. A bone nail of claim 3 wherein the bottom surface of said recess extends approximately in parallel with the side of said nail opposite said apex.

* * * * *